(12) United States Patent
Kameyama et al.

(10) Patent No.: US 7,361,922 B2
(45) Date of Patent: Apr. 22, 2008

(54) DIFFERENTIAL ABSORPTION LIDAR APPARATUS HAVING MULTIPLEXED LIGHT SIGNALS WITH TWO WAVELENGTHS IN A PREDETERMINED BEAM SIZE AND BEAM SHAPE

(75) Inventors: Shunpei Kameyama, Tokyo (JP); Yoshihito Hirano, Tokyo (JP)

(73) Assignee: Mitsubishi Electrick Corp., Tokyo (JP)

( * ) Notice: Subject to any disclaimer, the term of this patent is extended or adjusted under 35 U.S.C. 154(b) by 58 days.

(21) Appl. No.: 11/500,902

(22) Filed: Aug. 9, 2006

(65) Prior Publication Data

US 2007/0215795 A1    Sep. 20, 2007

(30) Foreign Application Priority Data

Mar. 14, 2006    (JP)    .............................. 2006-069286

(51) Int. Cl.
*G01N 15/06*    (2006.01)
(52) U.S. Cl. .................................... 250/574; 250/222.2
(58) Field of Classification Search ................ 250/573, 250/574, 559.4, 222.2, 221; 356/437, 436, 356/342, 338, 336
See application file for complete search history.

(56) References Cited

U.S. PATENT DOCUMENTS

| 6,509,566 B1 * | 1/2003 | Wamsley et al. ......... 250/338.5 |
| 2005/0146706 A1 | 7/2005 | Kameyama et al. |
| 2005/0162637 A1 | 7/2005 | Kameyama et al. |

FOREIGN PATENT DOCUMENTS

| JP | 2005-77347 A | 3/2005 |
| WO | WO-2004/061476 A1 | 12/2002 |
| WO | WO-2004-025324 A1 | 3/2004 |
| WO | WO-2004/074867 A1 | 9/2004 |

OTHER PUBLICATIONS

Grady J. Koch et al., Applied Optics, vol. 43, No. 26, Sep. 10, 2004, pp. 5092-5099.
Mark W. Phillips et al., 13th Coherent Laser Radar Conference, 2005, pp. 118-121.

* cited by examiner

*Primary Examiner*—Que T Le
(74) *Attorney, Agent, or Firm*—Birch, Stewart, Kolasch & Birch LLP

(57) ABSTRACT

A differential absorption lidar includes: a light signal generation unit for generating first, second CW light signals with first, second wavelengths having different absorption coefficients with respect to a target, a light intensity modulation unit for subjecting the first, second CW light signal to intensity modulation with a first, second CW modulation signal having a first, second frequency in a baseband, a radiation unit for multiplexing the first, second CW light signals with the intensity modulated, forming the multiplexed light signals with two wavelengths in a predetermined beam size, and radiating the light signals, a reception unit for directly detecting scattered light from the target and converting the scattered light into an electrical signal, and a signal processing unit for extracting only the first, second frequency components from the electric signal, and detecting the concentration of the target from a difference in an amplitude of time wavelengths between two signals.

9 Claims, 3 Drawing Sheets

DIFFERENTIAL ABSORPTION LIDAR APPARATUS HAVING MULTIPLEXED LIGHT SIGNALS WITH TWO WAVELENGTHS IN A PREDETERMINED BEAM SIZE AND BEAM SHAPE

BACKGROUND OF THE INVENTION

1. Field of the Invention

The present invention relates to a differential absorption lidar apparatus for transmitting laser light with at least two wavelengths in the air and receiving scattered light from a target (gas to be measured, such as carbon dioxide, ozone, or water vapor), and measuring the concentration of the target in the air from a difference in intensity of received light regarding each wavelength.

2. Related Background Art

A conventional differential absorption lidar apparatus transmits laser light with two wavelengths having very high coherency in the air, receives scattered light from the ground or an aerosol to be a target, and heterodyne-detects the received light and local light. The differential absorption lidar apparatus obtains a frequency spectrum of a signal obtained by heterodyne-detection, and detects received light regarding each of the two wavelengths from the frequency spectrum (see, for example, "Coherent differential absorption lidar measurements of $CO_2$" (edited by G. J. Koch et al., Applied Optics, Vol. 43, No. 26, 10 Sep. 2004, pp. 5092-5099) and "Coherent Laser Radar Transceiver for the NASA $CO_2$ Laser Absorption Spectrometer Instrument" (edited by M. W. Phillips et al., Proceedings of 13th Coherent Laser Radar Conference, 2005, pp. 118-121)).

At this time, among two wavelengths, one wavelength is set to be the one having a large absorption coefficient regarding gas to be measured, and the other wavelength is set to be the one having a small absorption coefficient. Owing to this setting, the amount of received light varies depending upon the concentration of gas to be measured between the apparatus and the target, and the concentration of the gas (specifically, the concentration of carbon gas) is measured from the difference.

The above-mentioned conventional differential absorption lidar apparatus is one type of a so-called coherent lidar. This type of lidar adopts a heterodyne-detection system that is likely to realize an ideal light reception state (a shot noise limit), and has an advantage in that a high S/N ratio is likely to be obtained in view of the reception, compared with an incoherent lidar known as the other type.

However, particularly in the case where the above-mentioned conventional differential absorption lidar apparatus is required to operate under very strict constraints (e.g., the apparatus is mounted on an artificial satellite to measure the concentration of gas in the vicinity of the ground), there arise the following problems.

First, in the coherent lidar, coherency at an optical carrier level of laser light to be transmitted/received is important, and it is also important to transmit/receive laser light having a very small line width. Furthermore, in order to perform a long-distance measurement of the order of 100 km as in the observation of the vicinity of the ground from the artificial satellite, a high transmission power of laser light is required. It is very difficult to allow laser light with such a small line width and a high power to be operated under strict constraints required when the coherent lidar is mounted on the satellite, which makes it difficult to maintain the reliability of the apparatus.

Furthermore, when a measurement is performed with the coherent lidar mounted on a moving body such as an artificial satellite, a Doppler frequency shift occurs in a light carrier due to the movement speed of the moving body itself. The Doppler frequency shift is 1.3 MHz with respect to the moving speed of 1 m/s, for example, in the case of an optical wavelength of 1.5 µm. That is, in view of the moving speed of the artificial satellite, a Doppler frequency shift of the order of 100 MHz may occur. However, it is difficult to successively grasp the Doppler frequency shift caused by the above-mentioned moving speed. Therefore, it is necessary to detect a component receiving an unknown frequency shift from a signal obtained by heterodyne-detection in a wide frequency range, which makes it difficult to detect a signal.

As described above, as a differential absorption lidar apparatus mounted on an artificial satellite required for satisfying strict constraints, the incoherent lidar is advantageous, which less requires a line width of laser light to be transmitted/received, and which is less influenced by a Doppler frequency shift.

However, assuming that the incoherent lidar adopts a pulse system (for example, transmits/receives a pulse corresponding to a distance resolution of about 150 m), a required reception bandwidth is about 1 MHz, and hence, a large reception bandwidth is required. According to a direct detection system used in light reception of the incoherent lidar, a reception S/N ratio is inversely proportional to the reception bandwidth. Thus, when the large reception bandwidth as described above is required, it is difficult to obtain a high reception S/N ratio.

Furthermore, if the incoherent lidar (see, for example, Technical Report 38 (edited by Murota et al., pp. 258-261, 2001 of Mitsubishi Heavy Industries Ltd.)) adopts a continuous wave (CW) system, a large bandwidth for responding to the above pulse is not required, so a reception bandwidth of a light receiver can be made small, and reception with high sensitivity becomes possible while direct detection is used in the light reception. However, this conventional differential absorption lidar apparatus has a problem regarding the function of receiving two wavelengths required for the apparatus. That is, the conventional differential absorption lidar apparatus has no function of identifying two wavelengths in reception, in the case where the incoherent lidar and the CW system are adopted, and two wavelengths are transmitted concurrently. Thus, if the CW system is used, there is no choice but to divide a timing for transmitting/receiving the two wavelengths in terms of the time, and transmit/receive them individually. According to such a configuration, in the case where the incoherent lidar mounted on an artificial satellite performs a measurement while moving, there arises the following problem.

In the case of a measurement while moving, according to the configuration in which two wavelengths are divided in terms of the time and transmitted/received individually, the irradiation position with respect to a target varies between two wavelength components. Generally, it is considered that the reflectance of a target varies depending upon the position. The differential absorption lidar apparatus measures the concentration of gas from the difference in the amount of received light between two wavelengths. Therefore, in order to perform a measurement with high precision, the dependence on only the difference in the amount of absorption in the air between two wavelengths is required as a precondition. When the reflectance varies in a measurement of the amount of received light at each wavelength, the precondition does not hold, which may degrade measurement precision.

For the above reasons, conventionally, in the measurement by the differential absorption lidar apparatus mounted on the artificial satellite required to satisfy strict constraints, the concentration of gas to be measured cannot be measured at a high reception S/N ratio and with high precision.

SUMMARY OF THE INVENTION

The present invention has been achieved to solve the above-mentioned problems, and has an object to obtain a differential absorption lidar apparatus capable of measuring the concentration of gas to be measured at a high reception S/N ratio and with high precision by applying an incoherent lidar of a CW system to the differential absorption lidar apparatus.

A differential absorption lidar apparatus according to the present invention includes: light signal generation means for generating a first CW light signal with a first wavelength having a large absorption coefficient regarding a target, and a second CW light signal with a second wavelength having a small absorption coefficient regarding the target; a first light intensity modulation means for subjecting the first CW light signal output from the light signal generation means to intensity modulation with a first CW modulation signal having a first frequency in a baseband, and subjecting the second CW light signal output from the light signal generation means to the intensity modulation with a second CW modulation signal having a second frequency in a baseband; radiation means for multiplexing the first and second CW light signals output and subjected to intensity modulation by the first light intensity modulation means, forming the multiplexed light signals with two wavelengths in a predetermined beam size and beam shape, and radiating the multiplexed light signals in an air; and reception means for directly detecting scattered light from the target present in the air and converting the scattered light into an electric signal; and signal processing means for extracting only components with the first and second frequencies from the electric signal output from the reception means, and detecting a concentration of the target from a difference in one of an amplitude and an electric power between the two signals.

DETAILED DESCRIPTION OF THE PREFERRED EMBODIMENTS

A differential absorption lidar apparatus according to the present invention exhibits an effect of allowing measurement of a concentration of gas to be measured at a high reception S/N ratio and with high precision.

Embodiment 1

Figure 1:
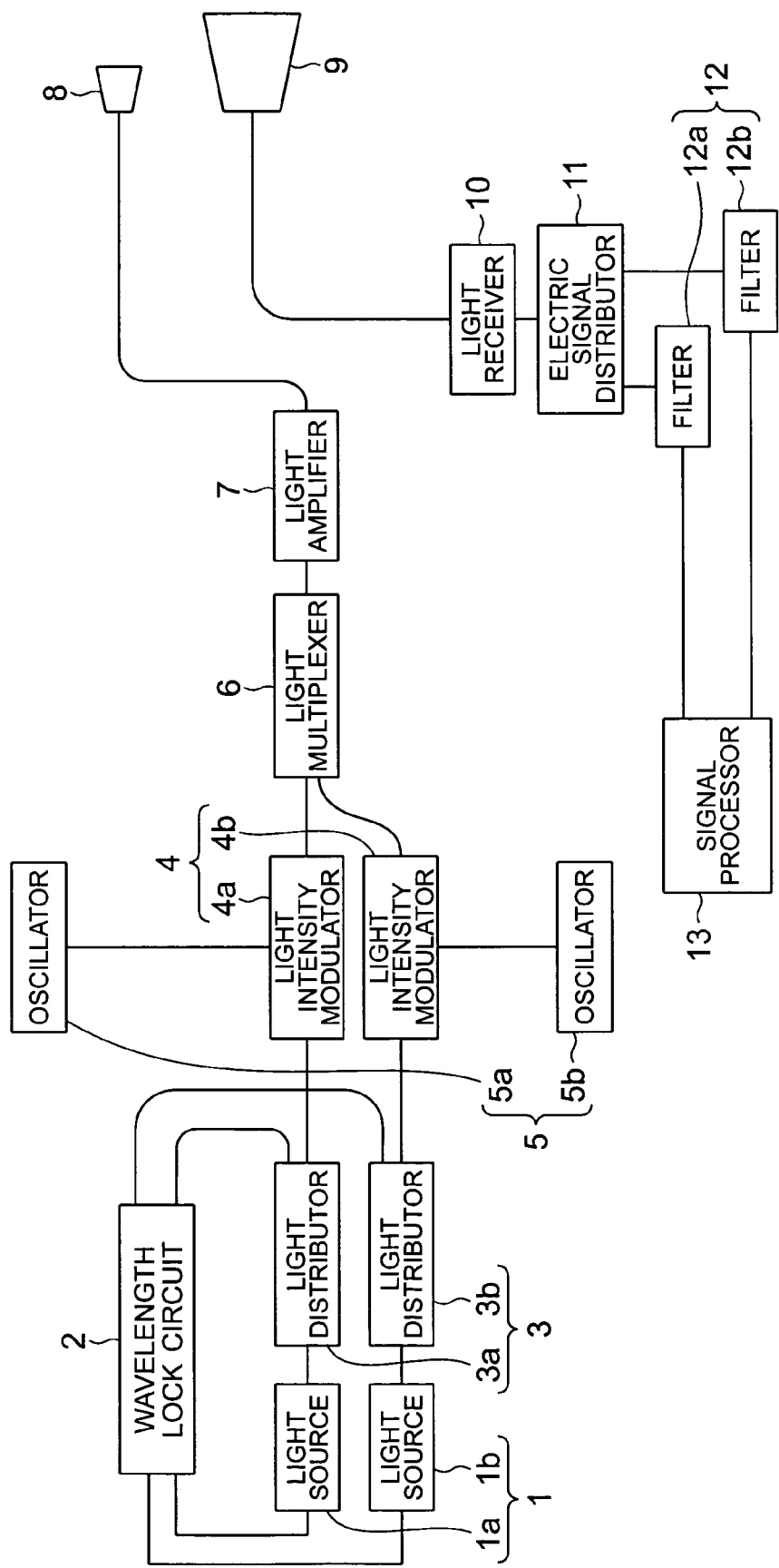
FIG. 1 is a block diagram showing a configuration of a differential absorption lidar apparatus according to Embodiment 1 of the present invention.

A differential absorption lidar apparatus according to Embodiment 1 of the present invention will be described with reference to FIG. 1. FIG. 1 is a block diagram showing a configuration of the differential absorption lidar apparatus according to Embodiment 1 of the present invention. Hereinafter, in each figure, like reference numerals denote like corresponding components.

In FIG. 1, the differential absorption lidar apparatus according to Embodiment 1 includes a light source 1 (1a and 1b), a wavelength lock circuit 2, a light distributor 3 (3a and 3b), a light intensity modulator 4 (4a and 4b), an oscillator 5 (5a and 5b), a light multiplexer 6, a light amplifier 7, a transmission optical system 8, a reception optical system 9, a light receiver 10, an electric signal distributor 11, a filter 12 (12a and 12b), and a signal processor 13.

The light source 1 (1a and 1b), the light distributor 3 (3a and 3b), and the wavelength lock circuit 2 constitute light signal generation means. Furthermore, the oscillator 5 (5a and 5b) and the light intensity modulator 4 (4a and 4b) constitute a first light intensity modulation means. Furthermore, the light multiplexer 6, the light amplifier 7, and the transmission optical system 8 constitute radiation means. Furthermore, the reception optical system 9 and the light receiver 10 constitute reception means. Furthermore, the electric signal distributor 11, the filter 12 (12a and 12b), and the signal processor 13 constitute signal processing means.

Furthermore, in FIG. 1, the light source 1a is connected to the light distributor 3a via an optical circuit line such as an optical fiber. Similarly, the light source 1b and the light distributor 3b, the light distributor 3a and the wavelength lock circuit 2, the light distributor 3a and the light intensity modulator 4a, the light distributor 3b and the wavelength lock circuit 2, the light distributor 3b and the light intensity modulator 4b, the light intensity modulator 4a and the light multiplexer 6, the light intensity modulator 4b and the light multiplexer 6, the light multiplexer 6 and the light amplifier 7, the light amplifier 7 and the transmission optical system 8, and the reception optical system 9 and the light receiver 10 are all connected via the optical circuit line such as an optical fiber.

The wavelength lock circuit 2 is connected to the light source 1a via an electric wire and a cable. Similarly, the wavelength lock circuit 2 and the light source 1b, the oscillator 5a and the light intensity modulator 4a, the oscillator 5b and the light intensity modulator 4b, the light receiver 10 and the electric signal distributor 11, the electric signal distributor 11 and the filter 12a, the electric signal distributor 11 and the filter 12b, the filter 12a and the signal processor 13, and the filter 12b and the signal processor 13 are all connected via the electric wire and the cable.

The two light sources 1a and 1b have a function of generating a CW light signal (laser light). At this time, the wavelength of light to be transmitted varies between the light sources 1a and 1b. Herein, it is assumed that the transmission wavelength of the light source 1a is λON, and the transmission wavelength of the light source 1b is λOFF. At this time, the transmission wavelength λON is set to be the wavelength having a large absorption coefficient (first absorption coefficient) with respect to the gas to be measured. Furthermore, the transmission wavelength λOFF is set to be the wavelength having a small absorption coefficient (second absorption coefficient) with respect to the gas to be measured. More specifically, there is a relationship: first absorption coefficient>second absorption coefficient.

Furthermore, the light distributor 3a has a function of distributing a light signal from the light source 1a, and transmitting one to the light intensity modulator 4a and the other to the wavelength lock circuit 2. Similarly, the light distributor 3b has a function of distributing a light signal from the light source 1b, and transmitting one to the light intensity modulator 4b and the other to the wavelength lock circuit 2.

The wavelength lock circuit 2 has a function of monitoring the wavelengths of the light signals from the light distributors 3a and 3b, and controlling the light sources 1a and 1b so that the wavelengths of transmitted light from the light sources 1a and 1b maintain desired values (i.e., λON and λOFF).

Furthermore, the oscillators 5a and 5b have a function of outputting CW electric signals respectively having two different frequencies fm1 and fm2, and transmitting the CW electric signals to the light intensity modulators 4a, 4b, respectively. Herein, the frequencies fm1 and fm2 are frequencies in respective basebands.

The light intensity modulators 4a and 4b have a function of modulating the intensity of the CW light signals from the light distributors 3a and 3b, based on modulation signals from the oscillators 5a and 5b.

The light multiplexer 6 has a function of multiplexing the light signals with the intensity modulated from the light intensity modulators 4a and 4b, and transmitting the light signals to the light amplifier 7. The light amplifier 7 has a function of amplifying the multiplexed light signals with two wavelengths from the light multiplexer 6, and transmitting the multiplexed light signals to the transmission optical system 8. The transmission optical system 8 has a function of forming the amplified light signals from the light amplifier 7 in a predetermined beam size and beam shape, and radiating the amplified light signals in the air.

On the other hand, the reception optical system 9 has a function of receiving scattered light from a target, combining the scattered light with the optical circuit line (herein, an optical fiber), and transmitting the resultant to the light receiver 10.

The light receiver 10 has a function of directly detecting the scattered light received from the target via the reception optical system 9, converting the scattered light into the electric signal, and transmitting the electric signal to the electric signal distributor 11. Furthermore, the electric signal distributor 11 has a function of distributing the electric signal from the light receiver 10, and transmitting one to the filter 12a and the other to the filter 12b, respectively.

The filters 12a and 12b have a function of filtering the signal from the electric signal distributor 11, and transmitting the signal to the signal processor 13. At this time, the filters 12a and 12b are band-pass filters capable of extracting only a predetermined frequency component. Regarding the filter 12a, the value of a frequency to be extracted is set to be the same (fm1) as that of a modulation signal frequency from the oscillator 5a. Regarding the filter 12b, the value of a frequency to be extracted is set to be the same (fm2) as that of a modulation signal frequency from the oscillator 5b.

Then, the signal processor 13 has a function of processing the filtered signals from the filters 12a and 12b, and obtaining the concentration of gas to be measured present in the atmosphere.

Next, the operation of the differential absorption lidar apparatus according to Embodiment 1 will be described with reference to the drawings.

First, the light sources 1a and 1b transmit CW light signals. At this time, as described above, the wavelength of light to be transmitted is λON regarding the light source 1a and λOFF regarding the light source 1b, which are different from each other.

Next, the light distributors 3a and 3b distribute the light signals from the light sources 1a and 1b, and transmit one to the light intensity modulators 4a and 4b, and the other to the wavelength lock circuit 2. At this time, the wavelength lock circuit 2 monitors the wavelengths of the light signals from the light distributors 3a and 3b, and controls the light sources 1a and 1b so that the wavelengths of transmitted light from the light sources 1a and 1b maintain desired values (i.e., λON and λOFF).

Next, the oscillators 5a and 5b output CW signals (electric signals) having two different frequencies fm1 and fm2, and transmit the CW signals to the light intensity modulators 4a and 4b, respectively. The light intensity modulators 4a and 4b modulate the intensity of the CW light signals from the light distributors 3a and 3b, based on the modulation signals from the oscillators 5a and 5b. Consequently, the intensity of the transmitted light having the wavelength λON from the light source 1a is modulated at the frequency fm1, and the intensity of the transmitted light having the wavelength of λOFF from the light source 1b is modulated at the frequency fm2.

Next, the light multiplexer 6 multiplexes the light signals with the intensity modulated from the light intensity modulators 4a and 4b, and transmit the light signals to the light amplifier 7. Then, the light amplifier 7 amplifies the multiplexed light signals with two wavelengths from the light multiplexer 6, and transmits the amplified light signals to the transmission optical system 8. Then, the transmission optical system 8 forms the amplified light signals from the light amplifier 7 in a predetermined beam size and beam shape, and radiates the light signals in the air. At this time, the light signals multiplexed by the light multiplexer 6 are amplified and radiated, which means that the light signals with two wavelengths λON and λOFF are radiated concurrently. Although the transmission powers of the light signals with two wavelengths radiated in the air are not required to be identical, for simplicity of the following description, it is assumed that the transmission powers are identical.

The light signals with two wavelengths radiated in the air have different absorption coefficients with respect to the gas to be measured, so there arises a difference in the amount of attenuation therebetween in the course of propagation in the air. Thus, the difference in the amount of attenuation is caused between the above-mentioned light signals with two wavelengths in the course of reciprocating propagation between the apparatus and the target. More specifically, even in the case of transmitting two wavelengths at the same transmission power, the difference in the amount of received light is also caused between the two wavelengths.

Then, the reception optical system 9 receives scattered light from the target, combines the scattered light with the optical circuit line (herein, an optical fiber), and transmits the light to the light receiver 10.

Next, the light receiver 10 directly detects the light received via the reception optical system 9, converts the light in to an electric signal, and transmits the electric signal to the electric signal distributor 11. At this time, an intensity signal of the received light is converted into the electric signal by direct detection. A component with the wavelength λON is modulated at the frequency fm1, and a component with the wavelength λOFF is modulated at the frequency fm2. Therefore, in the electric signal from the light receiver 10, the component with the wavelength λON has the frequency fm1, and the component with the wavelength λOFF has the frequency fm2.

As described above, the modulation frequencies fm1 and fm2 are frequencies in the base band. It is known that the transimpedance gain of the light receiver 10 can be set to a higher value by decreasing a reception frequency band.

Thus, by setting the modulation frequency as the baseband as in the present invention, the light reception sensitivity of the light receiver 10 is increased by enhancing the transimpedance gain thereof, and a high reception S/N ratio can be realized.

Next, the electric signal distributor 11 distributes the electric signal from the light receiver 10, and transmits one to the filter 12a and the other to the filter 12b, respectively. Then, the filters 12a and 12b filter the signals from the electric signal distributor 11, and transmit the filtered signals to the signal processor 13. At this time, the filters 12a and 12b are band-pass filters, which extract only a component with the frequency fm1 regarding the filter 12a and only a component with the frequency fm2 regarding the filter 12b. Therefore, the signal from the filter 12a becomes the component with the wavelength λON, and the signal from the filter 12b becomes the component with the wavelength λOFF.

Then, the signal processor 13 processes the filtered signals from the filters 12a and 12b.

Specifically, two signals from the two filters 12a and 12b are A/D (analog/digital) converted, respectively. Consequently, the time wavelengths of two digital signals become signals with the frequencies fm1 and fm2. Next, amplitudes or electric powers of the time wavelengths are compared. In the case where there is almost no gas to be measured in the air between the apparatus and the target, the two wavelengths are hardly influenced by absorption in the course of propagation in the air, so the amplitudes or the electric powers of the two time wavelengths become substantially the same.

In contrast, in the case where gas to be measured is present in a large concentration in the air between the apparatus and the target, the two wavelengths are greatly influenced by absorption in the course of propagation in the air, and accordingly, the amplitudes of the two time wavelengths vary greatly. Specifically, the amplitude or the electric power of the time wavelength of the component with the frequency fm1 corresponding to the wavelength λON becomes remarkably small, compared with the amplitude or the electric power of the time wavelength of the component with the frequency fm2 corresponding to the wavelength λOFF. The difference in the amplitude or the electric power of the time wavelengths can be associated with the difference in the amount of received light between two wavelengths. The difference in the amount of received light can be associated with the difference in the amount of absorption with respect to the gas to be measured in the air between two wavelengths. Furthermore, the difference in the amount of absorption can be associated with the concentration of gas in the air. Thus, the concentration of gas to be measured in the air can be detected from the difference in the amplitude or the electric power of the time wavelengths.

That is, the differential absorption lidar apparatus according to Embodiment 1 includes the first light source 1a for generating a first CW light signal with a first wavelength (λON) having a large absorption coefficient with respect to a target (gas to be measured), the second light source 1b for generating a second CW light signal with a second wavelength (λOFF) having a small absorption coefficient with respect to the target, the first light distributor 3a for distributing the first CW light signal output from the first light source 1a, the second light distributor 3b for distributing the second CW light signal output from the second light source 1b, the wavelength lock circuit 2 for monitoring the wavelengths of the first and second CW light signals output from the first and second light distributors 3a, 3b, and controlling the first and second light sources 1a and 1b so that the first and second CW light signals maintain the first and second wavelengths, the first oscillator 5a for outputting a first CW modulation signal with a first frequency (fm1) in a baseband, the second oscillator 5b for outputting a second CW modulation signal with a second frequency (fm2) in a baseband, the first light intensity modulator 4a for subjecting the first CW light signal output from the first light distributor 3a to intensity modulation with the first CW modulation signal, the second light intensity modulator 4b for subjecting the second CW light signal output from the second light distributor 3b to intensity modulation with the second CW modulation signal, the light multiplexer 6 for multiplexing the first and second CW light signals output and subjected to intensity modulation by the first and second light intensity modulators 4a and 4b, the light amplifier 7 for amplifying the light signals with two wavelengths output and multiplexed by the light amplifier 6, and the transmission optical system 8 for forming the light signals with two wavelengths output and amplified by the light amplifier 7 in a predetermined beam size and beam shape and radiating the light signals in the air.

The differential absorption lidar apparatus according to Embodiment 1 further includes the reception optical system 9 for receiving scattered light from the target present in the air, the light receiver 10 for directly detecting the scattered light output from the reception optical system 9 and converting the scattered light into an electric signal, the electric signal distributor 11 for distributing the electric signal output from the light receiver 10, the first filter 12a for extracting only a component with the first frequency (fm1) from the electric signal output and distributed by the electric signal distributor 11, the second filter 12b for extracting only a component with the frequency (fm2) from the electric signal output and distributed by the electric signal distributor 11, and the signal processor 13 for converting two signals output from the first and second filters 12a and 12b into digital signals, and detecting the concentration of the target from the difference in the amplitude or the electric power between time wavelengths of the two digital signals.

The differential absorption lidar apparatus according to Embodiment 1 as described above transmits/receives light signals with two wavelengths λON and λOFF concurrently. Thus, for example, even in the case where the differential absorption lidar apparatus is mounted on a moving body such as an artificial satellite, a radiation spot on a target of the radiated light signal varies successively, and the reflectance of the target varies successively, components with two wavelengths are always radiated at the same spot, i.e., positions with the same reflectance. Therefore, even in the case where the differential absorption lidar apparatus is mounted on the moving body, the concentration of the gas to be measured can be detected with high precision.

Furthermore, the differential absorption lidar apparatus according to Embodiment 1 uses the frequency in the baseband for transmission light. Therefore, the transimpedance gain in the light receiver 10 can be enhanced, and the measurement can be performed at a high reception S/N ratio. Accordingly, the concentration of the gas can be detected with higher precision.

Furthermore, the differential absorption lidar apparatus according to Embodiment 1 uses the frequency in the baseband for transmission light and uses direct detection for a light reception method. Therefore, even in the case where the differential absorption lidar apparatus is mounted on the moving body such as an artificial satellite, and the distance between the apparatus and the target varies, the influence of a Doppler frequency shift is small. Specifically, in the case where the apparatus is moving at a relative speed of 10 m/s with respect to the target, the Doppler frequency shift of the order of MHz occurs regarding an optical wavelength. Therefore, in the case of using heterodyne detection for the light reception method, the light receiver in a large frequency band of the order of MHz is required accordingly. This makes it necessary to decrease the transimpedance gain, with the result that only low reception sensitivity is obtained. However, in Embodiment 1, if the frequencies fm1 and fm2 are set to be about kHz, the Doppler frequency shift corresponding to a relative speed becomes a value lower by 10 orders of magnitude with respect to the order of MHz, which can be almost ignored. Along with this, even in the case where the differential absorption lidar apparatus is mounted on the moving body, the transimpedance gain of the light receiver 10 can be kept high.

In the differential absorption lidar apparatus according to Embodiment 1 described above, the electric signals from the light receiver 10 are distributed in two by the electric signal distributor 11, and predetermined frequency components are extracted by the first and second filters 12a and 12b, and taken in the signal processor 13. However, the electric signal from the light receiver 10 may be directly taken in the signal processor 13 to be A/D converted. In this case, the signal processor 13 has spectrum analysis means such as an FFT. In the signal processor 13, the frequency spectrum of the electric signal from the light receiver 10 is calculated, predetermined frequency components (herein, fm1 and fm2 components) on the frequency spectrum are detected, and the concentration of the gas to be measured is detected from the difference in the amplitude or the electric power of the frequency components. According to such a configuration, the electric signal distributor 11 and the first and second filters 12a and 12b can be removed to simplify the configuration of the apparatus, whereby an effect of realizing further miniaturization and reduction in weight is obtained.

Embodiment 2

Figure 2:
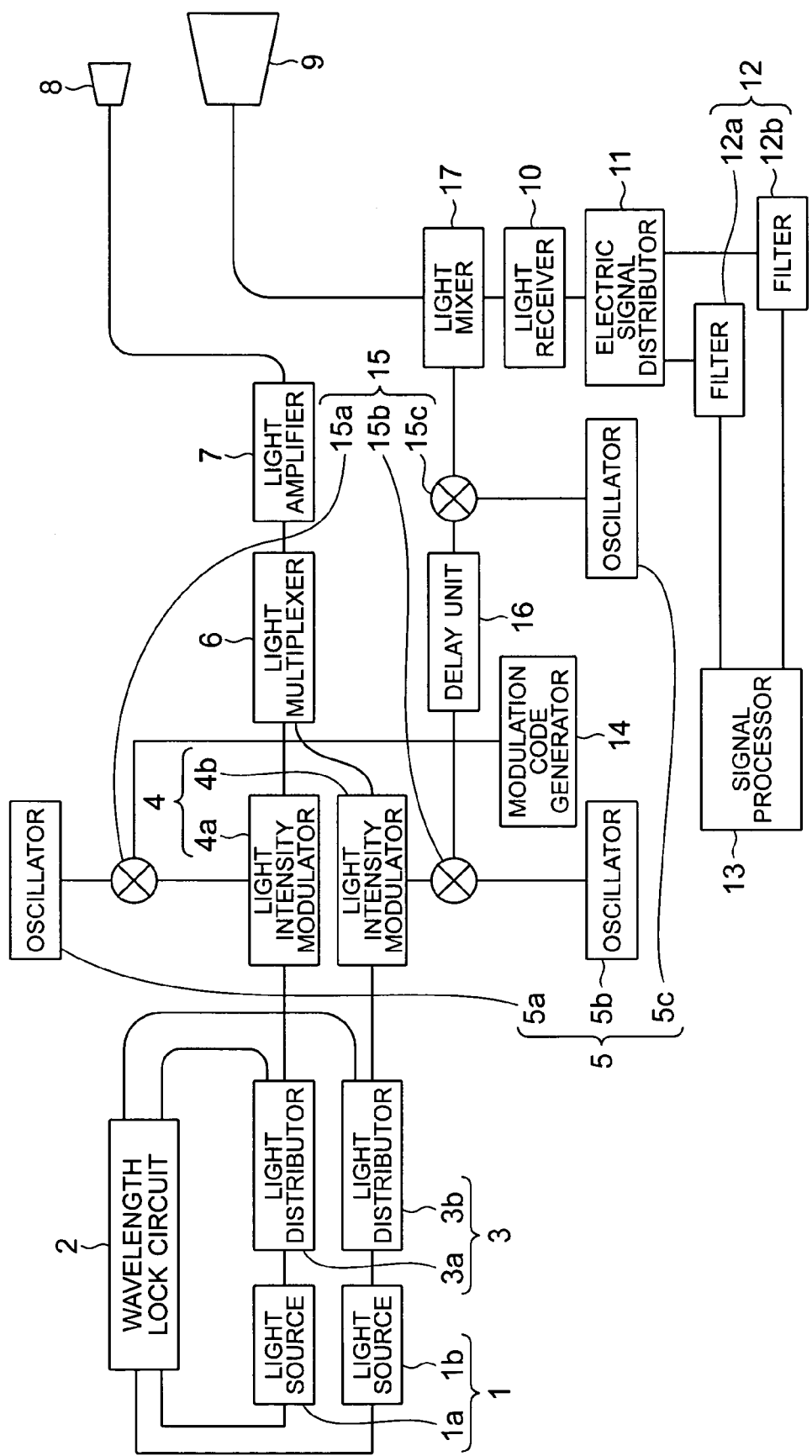
FIG. 2 is a block diagram showing a configuration of a differential absorption lidar apparatus according to Embodiment 2 of the present invention.

A differential absorption lidar apparatus according to Embodiment 2 of the present invention will be described with reference to FIGS. 2 and 3. FIG. 2 is a block diagram showing a configuration of the differential absorption lidar apparatus according to Embodiment 2 of the present invention.

In FIG. 2, the differential absorption lidar apparatus according to Embodiment 2 includes a modulation code generator 14, an electric mixer 15 (15a, 15b, and 15c), a delay unit 16, and a light mixer 17, in addition to the above-mentioned components of the differential absorption lidar apparatus in Embodiment 1.

Furthermore, although there are two oscillators 5 in Embodiment 1, there are three oscillators 5 (5a, 5b, and 5c) in Embodiment 2. The other components are the same as those shown in Embodiment 1.

The light source 1 (1a and 1b), the light distributor 3 (3a and 3b), and the wavelength lock circuit 2 constitute the light signal generation means. Furthermore, the oscillator 5 (5a and 5b), the modulation code generator 14, the electric mixer 15 (15a and 15b), and the light intensity modulator 4 (4a and 4b) constitute a second light intensity modulation means. Furthermore, the light multiplexer 6, the light amplifier 7, and the transmission optical system 8 constitute the radiation means. Furthermore, the reception optical system 9, the oscillator 5c, the delay unit 16, the electric mixer 15c, the light mixer 17, and the light receiver 10 constitute reception demodulation means. Furthermore, the electric signal distributor 11, the filter 12 (12a and 12b), and the signal processor 13 constitute the signal processing means.

The modulation code generator 14 is connected to the electric mixers 15a and 15b, and the delay unit 16. The electric mixer 15a is connected under the condition of being inserted between the oscillator 5a and the light intensity modulator 4a. Similarly, the electric mixer 15b is connected under the condition of being inserted between the oscillator 5b and the light intensity modulator 4b. The delay unit 16 is connected under the condition of being inserted between the electric mixers 15b and 15c. The electric mixer 15c is connected to the oscillator 5c and the light mixer 17. The light mixer 17 is connected under the condition of being inserted between the reception optical system 9 and the light receiver 10.

Furthermore, the modulation code generator 14 and the electric mixer 15a are connected to each other via electric wire and cable. Similarly, the modulation code generator 14 and the electric mixer 15b, the modulation code generator 14 and the delay unit 16, the electric mixer 15a and the oscillator 5a, the electric mixer 15a and the light intensity modulator 4a, the electric mixer 15b and the oscillator 5b, the electric mixer 15b and the light intensity modulator 4b, the delay unit 16 and the electric mixer 15c, the electric mixer 15c and the oscillator 5c, and the electric mixer 15c and the light mixer 17 are all connected via electric wire and cable.

On the other hand, the light mixer 17 and the reception optical system 9, and the light mixer 17 and the light receiver 10 are connected via the optical circuit line (specifically, an optical fiber). The other connections are the same as those shown in Embodiment 1.

In FIG. 2, the oscillators 5a, 5b, and 5c have a function of generating CW electric signals respectively, and transmitting the CW electric signals to the electric mixers 15a, 15b, and 15c. In Embodiment 1, the modulation signal frequencies from the oscillators 5a and 5b are fm1 and fm2 in the baseband. However, in Embodiment 2, the frequencies are fm+fm1 and fm+fm2. Furthermore, the frequency of a signal generated from the oscillator 5c is fm. Herein, fm1 and fm2 are frequencies in a baseband of, for example, about 1 kHz in the same way as in Embodiment 1, and fm is a frequency in a microwave band of, for example, about 100 MHz.

The modulation code generator 14 has a function of generating a modulation code from a pseudo random series (e.g., an M series) having a predetermined code width, and transmitting the modulation code to the electric mixers 15a, 15b, and the delay unit 16. The delay unit 16 has a function of delaying the modulation code from the modulation code generator 14, and transmitting the modulation code to the electric mixer 15c. The electric mixers 15a, 15b, and 15c have a function of further subjecting the signals from the oscillators 5a, 5b, and 5c to modulation (e.g., BPSK (Binary Phase Shift Keying: 2-phase modulation)) based on the input modulation code, and transmitting the modulated signals to the light intensity modulators 4a and 4b as modulation signals, and to the light mixer 17 as a demodulation signal, respectively.

The light mixer 17 has a function of demodulating the frequency of intensity modulation of the light received at the reception optical system 9, based on the input demodulation signal.

Next, the operation of the differential absorption lidar apparatus according to Embodiment 2 will be described with reference to the drawings. FIG. 3 illustrates the operation of the differential absorption lidar apparatus according to Embodiment 2.

First, the light sources 1a and 1b transmit CW light signals with two wavelengths in the same way as in Embodiment 1.

Next, same as Embodiment 1, the light distributors 3a and 3b distribute the light signals from the light sources 1a and 1b, and transmit one to the light intensity modulators 4a and 4b, and the other to the wavelength lock circuit 2. At this time, the wavelength lock circuit 2 controls the light sources 1a and 1b so that the wavelengths of the transmitted light from the light sources 1a and 1b maintain desired values (i.e., λON and λOFF) as in Embodiment 1.

Next, the oscillators 5a, 5b, and 5c output CW signals (electric signals) with frequencies fm+fm1, fm+fm2, and fm different from each other. Further more, the modulation code generator 14 generates a pseudo random series signal (herein, an M series signal) having a predetermined code width (herein, Δt).

Figure 3:
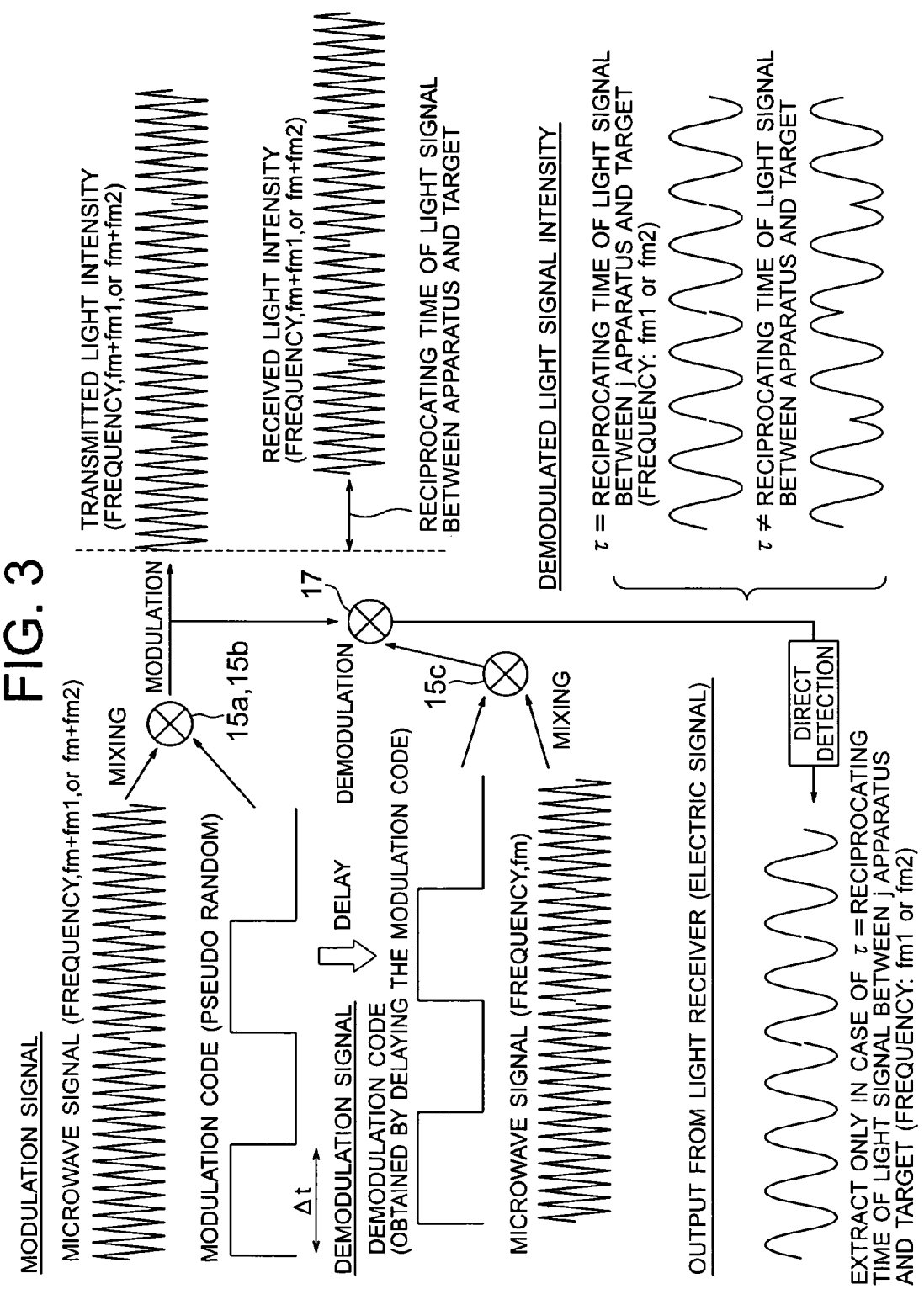
FIG. 3 is a diagram illustrating an operation of the differential absorption lidar apparatus according to Embodiment 2 of the present invention.

As shown in FIG. 3, the electric mixers 15a and 15b mix the signals from the oscillators 5a and 5b with the signal from the modulation code generator 14 to generate modulation signals subjected to BPSK, with the frequencies fm+fm1 and fm+fm2 and the code width Δt, and transmits the modulation signals to the light intensity modulators 4a and 4b.

Furthermore, the delay unit 16 outputs a signal delayed by a time τ with respect to the input modulation code. As shown in FIG. 3, the electric mixer 15c mixes the signal from the oscillator 5c with the signal from the delay unit 16 to generate a demodulation signal subjected to BPSK, with the frequency fm and the code width Δt, and transmit the demodulation signals to the light mixer 17.

The light intensity modulators 4a and 4b modulate the intensity of the CW light signals from the light distributors 3a and 3b, based on the signals from the electric mixers 15a and 15b. Consequently, referring to FIG. 3, the intensity of the transmitted light having the wavelength λON from the light source 1a is subjected to BPSK for intensity modulation at the frequency fm+fm1 and the code width Δt, and the intensity of the transmitted light having the wavelength of λOFF from the light source 1b is subjected to BPSK for intensity modulation at the frequency fm+fm2 and the code width ΔΔt.

Next, the light multiplexer 6 multiplexes the light signals subjected to BPSK for intensity modulation, from the light intensity modulators 4a and 4b, and transmits the modulated light signals to the light amplifier 7 as in Embodiment 1. Then, the light amplifier 7 amplifies the multiplexed light signals with two wavelengths from the light multiplexer 6, and transmits the amplified light signals to the transmission optical system 8 as in Embodiment 1. Then, the transmission optical system 8 forms the amplified light signals from the light amplifier 7 in a predetermined beam size and beam shape, and radiates the light signals in the air as in Embodiment 1. At this time, the light signals multiplexed by the light multiplexer 6 are amplified and radiated, which means that the light signals with two wavelengths λON and λOFF are radiated concurrently as in Embodiment 1.

On the other hand, the reception optical system 9 receives the scattered light from the target, combines the scattered light with the optical circuit line (herein, an optical fiber), and transmits the resultant to the light mixer 17.

Then, the light mixer 17 demodulates the frequency of the intensity modulation of the light received at the reception optical system 9, based on the demodulation signal input from the electric mixer 15c, and transmits the demodulated light signal to the light receiver 10. At this time, as shown in FIG. 3, the frequency of the intensity modulation of the light signal output from the light mixer 17 becomes a frequency of a difference between the intensity modulation frequency of the light received from the reception optical system 9 and the demodulation signal frequency input from the electric mixer 15c. That is, the frequency is (fm+fm1)−fm=fm1 regarding the component of the wavelength λON, and (fm+fm2)−fm=fm2 regarding the component with the wavelength λOFF.

Furthermore, the modulation signal and the demodulation signal are subjected to BPSK modulation. Thus, as shown in FIG. 3, in the case where the delay time τ given by the delay unit 16 is the same as the light signal reciprocating time between the apparatus and the target, ideal demodulation is performed, and a waveform of the intensity modulation of the light signal from the light mixer 17 becomes an ideal sinusoidal wave with the frequencies fm1 and fm2. In contrast, as shown in FIG. 3, in the case where the delay time τ is not the same as the light signal reciprocating time between the apparatus and the target, the ideal demodulation is not performed. Therefore, the waveform of the intensity modulation of the light signal from the light mixer 17 becomes a random waveform subjected to pseudo random modulation on the code width Δt basis.

Next, the light receiver 10 directly detects the light signal demodulated by the light mixer 17, converts the light signal into an electric signal, and transmits the electric signal to the electric signal distributor 11. At this time, the intensity signal of the received light is converted into an electric signal by direct detection. The reception bandwidth of the light receiver 10 is limited to the baseband in the same way as in Embodiment 1. By doing so, in the case where the delay time τ is the same as the light reciprocating time between the apparatus and the target and the ideal demodulation is performed in the light mixer 17, the intensity modulation components of the baseband frequencies fm1 and fm2 are extracted. In contrast, in the case where the delay time τ is different from the light reciprocating time between the apparatus and the target, the waveform of the intensity modulation of the light signal becomes a random waveform subjected to pseudo random modulation on the code width Δt basis. If the value of 1/Δt is set to be a sufficiently large value with respect to the reception bandwidth of the light receiver 10, as shown in FIG. 3, the random component, i.e., the component in which the reciprocating time of a light signal of the distance between the apparatus and the target is not the same as the delay time τ, is not extracted.

Then, the signal from the light receiver 10 is distributed, filtered, and processed in the same way as in Embodiment 1, whereby the concentration of the gas to be measured can be obtained.

That is, the differential absorption lidar apparatus according to Embodiment 2 includes the first light source 1a for generating the first CW light signal with the first wavelength (λON) having a large absorption coefficient with respect to the target (gas to be measured), the second light source 1b for generating the second CW light signal with the second wavelength (λOFF) having a small absorption coefficient with respect to the target, the first light distributor 3a for distributing the first CW light signal output from the first light source 1a, the second light distributor 3b for distributing the second CW light signal output from the second light source 1b, the wavelength lock circuit 2 for monitoring the wavelengths of the first and second CW light signals output from the first and second light distributors 3a and 3b, and controlling the first and second light sources 1a and 1b so that the wavelengths of the first and second CW light sources 1a and 1b are kept to be the first and second wavelengths, the first oscillator 5a for outputting the first CW electric signal with the frequency (fm+fm1) containing the first frequency (fm1) in the baseband and the frequency (fm) in the microwave band, the second oscillator 5b for outputting the second CW electric signal-with the frequency (fm+fm2) containing the second frequency (fm2) in the baseband and the frequency (fm) in the microwave band, the modulation code generator 14 for generating a modulation code that is a pseudo random series with a predetermined code width (Δt), the first electric mixer 15a for subjecting the first CW electric signal output from the first oscillator 5a to BPSK modulation with the modulation code, and outputting the modulated signal as the first modulation signal, the second electric mixer 15b for subjecting the second CW electric signal output from the second oscillator 5b to BPSK modulation with the modulation code, and outputting the modulated signal as the second modulation signal, the first light intensity modulator 4a for subjecting the first CW light signal output from the first light distributor 3a to intensity modulation with the first modulation signal, the second light intensity modulator 4b for subjecting the second CW light signal output from the second light distributor 3b to intensity modulation with the second modulation signal, the light multiplexer 6 for multiplexing the first and second CW light signals output and subjected to intensity modulation by the first and second light intensity modulators 4a and 4b, the light amplifier 7 for amplifying the light signals with two wavelengths output and multiplexed by the light multiplexer 6, and the transmission optical system 8 for forming the light signals with two wavelengths output and amplified by the light amplifier 7 in a predetermined beam size and beam shape, and radiating the formed light signals in the air.

The differential absorption lidar apparatus according to Embodiment 2 further includes the reception optical system 9 for receiving the scattered light from the target present in the air, the third oscillator 5c for outputting the third CW electric signal with the frequency (fm) in the microwave band, the delay unit 16 for delaying the modulation code output from the modulation code generator 14 by the same time (τ) as the light signal reciprocating time between the apparatus and the target, the third electric mixer 15c for subjecting the third CW electric signal output from the third oscillator 5c to BPSK modulation with the delayed modulation code and outputting the modulated CW electric signal as the demodulation signal, the light mixer 17 for demodulating the frequency of the intensity modulation of the scattered light output from the reception optical system 9 based on the demodulation signal, the light receiver 10 for directly detecting the light signal output and demodulated by the light mixer 17 and converting the light signal into an electric signal, the electric signal distributor 11 for distributing the electric signal output from the light receiver 10, the first filter 12a for extracting only the component with the first frequency (fm1) from the electric signal output and distributed by the electric signal distributor 11, the second filter 12b for extracting only the component with the second frequency (fm2) from the electric signal output and distributed by the electric signal distributor 11, and the signal processor 13 for converting the two signals output from the first and second filters 12a and 12b into digital signals, and detecting the concentration of the target from the difference in the amplitude or the electric power of the time wavelengths of the two digital signals.

In Embodiment 1, in the case where light received from a plurality of targets at a plurality of distances are overlapped, only a received light component from a particular target cannot be extracted. However, in Embodiment 2, if the delay time τ is set to be the same as the reciprocating time of a light signals up to a desired target, the received light from the desired target and the received light from another target can be discriminated. Furthermore, if delay time varying means for varying a delay time is provided, the delay time is varied successively, and a delay time at which the amplitude of the signal output from the light receiver 10 increases is searched for, whereby the respective distances of the plurality of targets at plurality of distances can be known. Furthermore, for example, even in the case where the differential absorption lidar apparatus according to Embodiment 2 is mounted on the moving body such as an artificial satellite to perform a measurement, and the distance between the apparatus and the target varies successively, the ideal demodulation can always be performed with respect to the received light from the desired target by using a function of successively varying the delay time.

The differential absorption lidar apparatus according to Embodiment 2 described above may have the following configuration, in the same way as described in Embodiment 1: the electric signal from the light receiver 10 is directly taken in the signal processor 13 and A/D converted, whereby the concentration of gas to be measured is detected using the spectrum analysis means. With such a configuration, for the same reason as described in Embodiment 1, the effect of simplifying the configuration of the apparatus to realize further miniaturization and reduction in weight is obtained.

What is claimed is:

1. A differential absorption lidar apparatus, comprising:
light signal generation means for generating a first CW light signal with a first wavelength having a large absorption coefficient regarding a target, and a second CW light signal with a second wavelength having a small absorption coefficient regarding the target;
a first light intensity modulation means for subjecting the first CW light signal output from the light signal generation means to intensity modulation with a first CW modulation signal having a first frequency in a baseband, and subjecting the second CW light signal output from the light signal generation means to the intensity modulation with a second CW modulation signal having a second frequency in a baseband;
radiation means for multiplexing the first and second CW light signals output and subjected to intensity modulation by the first light intensity modulation means, forming the multiplexed light signals with two wavelengths in a predetermined beam size and beam shape, and radiating the multiplexed light signals in an air; and
reception means for directly detecting scattered light from the target present in the air and converting the scattered light into an electric signal; and
signal processing means for extracting only components with the first and second frequencies from the electric signal output from the reception means, and detecting a concentration of the target from a difference in one of an amplitude and an electric power between the two signals.

2. A differential absorption lidar apparatus according to claim 1, wherein:
the light signal generation means comprises:
a first light source for generating the first CW light signal with the first wavelength having a large absorption coefficient regarding the target;

a second light source for generating the second CW light signal with the second wavelength having a small absorption coefficient regarding the target;
a first light distributor for distributing the first CW light signal output from the first light source;
a second light distributor for distributing the second CW light signal output from the second light source; and
a wavelength lock circuit for monitoring wavelengths of the first and second CW light signals output from the first and second light distributors, respectively, and controlling the first and second light sources so that the first and second CW light signals maintain the first and second wavelengths, respectively;
the first light intensity modulation means comprises:
a first oscillator for outputting the first CW modulation signal with the first frequency in the baseband;
a second oscillator for outputting the second CW modulation signal with the second frequency in the baseband;
a first light intensity modulator for subjecting the first CW light signal output from the first light distributor to intensity modulation with the first CW modulation signal; and
a second light intensity modulator for subjecting the second CW light signal output from the second light distributor to intensity modulation with the second CW modulation signal;
the radiation means comprises:
a light multiplexer for multiplexing the first and second CW light signals output and subjected to intensity modulation by the first and second light intensity modulators, respectively;
a light amplifier for amplifying the light signals with two wavelengths output and multiplexed by the light multiplexer; and
a transmission optical system for forming the light signals with two wavelengths output and amplified by the light amplifier in a predetermined beam size and beam shape, and radiating the light signals in the air; and
the reception means comprises:
a reception optical system for receiving scattered light from the target present in the air; and
a light receiver for directly detecting the scattered light output from the reception optical system and converting the scattered light into an electric signal.

3. A differential absorption lidar apparatus according to claim 1, wherein the signal processing means comprises:
an electric signal distributor for distributing an electric signal output from the light receiver;
a first filter for extracting only the component with the first frequency from the electric signal output and distributed by the electric signal distributor;
a second filter for extracting only the component with the second frequency from the electric signal output and distributed by the electric signal distributor; and
a signal processor for detecting a concentration of the target from the difference in one of the amplitude and the electric power between the two signals output from the first and second filters.

4. A differential absorption lidar apparatus according to claim 1, wherein the signal processing means comprises a signal processor for calculating a frequency spectrum of an electric signal output from the light receiver, and detecting a concentration of the target from the difference in one of the amplitude and the electric power on the frequency spectrum between the components with the first and second frequencies.

5. A differential absorption lidar apparatus, comprising:
light signal generation means generating a first CW light signal with a first wavelength having a large absorption coefficient regarding a target, and a second CW light signal with a second wavelength having a small absorption coefficient regarding the target;
a second light intensity modulation means for subjecting a first CW electric signal with a frequency containing a first frequency in a baseband and a frequency in a microwave band to BPSK modulation with a modulation code that is a pseudo random series with a predetermined code width to generate a first modulation signal, subjecting a second CW electric signal with a frequency containing a second frequency in a baseband and the frequency in a microwave band to BPSK modulation with the modulation code to generate a second modulation signal, subjecting the first CW light signal output from the light signal generation means to intensity modulation with the first modulation signal, and subjecting the second CW light signal output from the light signal generation means to intensity modulation with the second modulation signal;
radiation means for multiplexing the first and second CW light signals output and subjected to intensity modulation by the second light intensity modulation means, forming the multiplexed light signals with two wavelengths in a predetermined beam size and beam shape, and radiating the light signals in an air;
reception demodulation means for subjecting a third CW electric signal with the frequency in a microwave band to modulation with the modulation code delayed by the same amount of time as a light signal reciprocating time between the apparatus and the target to generate a demodulation signal, demodulating a frequency of intensity modulation of scattered light from the target present in the air, directly detecting the demodulated light signal, and converting the light signal into an electric signal; and
signal processing means for extracting only components with the first and second frequencies respectively from the electric signal output from the reception demodulation means, and detecting a concentration of the target from a difference in one of an amplitude and an electric power between the two signals.

6. A differential lidar apparatus according to claim 5, further comprising delay time varying means for varying a delay time of the modulation code.

7. A differential absorption lidar apparatus according to claim 5, wherein:
the light signal generation means comprises:
a first light source for generating the first CW light signal with the first wavelength having a large absorption coefficient regarding the target;
a second light source for generating the second CW light signal with the second wavelength having a small absorption coefficient regarding the target;
a first light distributor for distributing the first CW light signal output from the first light source;
a second light distributor for distributing the second CW light signal output from the second light source; and
a wavelength lock circuit for monitoring wavelengths of the first and second CW light signals output from the first and second light distributors, respectively, and controlling the first and second light sources so that the first and second CW light signals maintain the first and second wavelengths, respectively;

the second light intensity modulation means comprises:
- a first oscillator for outputting the first CW electric signal with a frequency containing the first frequency in the baseband and the frequency in the microwave band;
- a second oscillator for outputting the second CW electric signal with a frequency containing the second frequency in the baseband and the frequency in the microwave band;
- a modulation code generator for generating a modulation code that is a pseudo random series with a predetermined code width;
- a first electric mixer for subjecting the first CW electric signal output from the first oscillator to BPSK modulation with the modulation code to output the first CW electric signal as the first modulation signal;
- a second electric mixer for subjecting the second CW electric signal output from the second oscillator to BPSK modulation with the modulation code to output the second CW electric signal as the second modulation signal;
- a first light intensity modulator for subjecting the first CW light signal output from the first light distributor to intensity modulation with the first modulation signal; and
- a second light intensity modulator for subjecting the second CW light signal output from the second light distributor to intensity modulation with the second modulation signal;

the radiation means comprises:
- a light multiplexer for multiplexing the first and second CW light signals output and subjected to intensity modulation by the first and second light intensity modulators, respectively;
- a light amplifier for amplifying the light signals with two wavelengths output and multiplexed by the light multiplexer; and
- a transmission optical system for forming the light signals with two wavelengths output and amplified by the light amplifier in a predetermined beam size and beam shape, and radiating the light signals in the air, respectively; and the reception demodulation means comprises:
- a reception optical system for receiving scattered light from the target present in the air;
- a third oscillator for outputting the third CW electric signal with the frequency in the microwave band;
- a delay unit for delaying the modulation code output from the modulation code generator by the same amount of time as the light signal reciprocating time between the apparatus and the target;
- a third electric mixer for subjecting the third CW electric signal output from the third oscillator to BPSK modulation with the delayed modulation code to output the third CW electric signal as the demodulation signal;
- a light mixer for demodulating the frequency of intensity modulation of scattered light output from the reception optical system based on the demodulation signal; and
- a light receiver for directly detecting the light signal output and demodulated by the light mixer and converting the light signal into an electric signal.

8. A differential absorption lidar apparatus according to claim 5, wherein the signal processing means comprises:
- an electric signal distributor for distributing an electric signal output from the light receiver;
- a first filter for extracting only the component with the first frequency from the electric signal output and distributed by the electric signal distributor;
- a second filter for extracting only the component with the second frequency from the electric signal output and distributed by the electric signal distributor; and
- a signal processor for detecting a concentration of the target from the difference in one of the amplitude and the electric power between the two signals output from the first and second filters.

9. A differential absorption lidar apparatus according to claim 5, wherein the signal processing means comprises a signal processor for calculating a frequency spectrum of an electric signal output from the light receiver, and detecting a concentration of the target from the difference in one of the amplitude and the electric power on the frequency spectrum between the components with the first and second frequencies.

* * * * *